United States Patent [19]

Connor et al.

[11] Patent Number: 5,210,204

[45] Date of Patent: May 11, 1993

[54] BIPHENYL OXADIAZOLES AND THIADIAZOLES AS ANGIOTHESIN II ANTAGONISTS

[75] Inventors: David T. Connor, Ann Arbor; Catherine R. Kostlan, Saline, both of Mich.

[73] Assignee: Warner-Lambert Company, Morris Plains, N.J.

[21] Appl. No.: 899,395

[22] Filed: Jun. 16, 1992

[51] Int. Cl.⁵ .................. C07D 271/10; C07D 285/12
[52] U.S. Cl. .................................. 548/144; 548/132; 548/136; 546/118; 546/153; 546/277; 544/284; 544/319
[58] Field of Search .................. 548/144, 132, 136; 546/118, 153, 277; 544/284, 319; 514/256, 259, 312, 340, 342, 363, 364

[56] References Cited

U.S. PATENT DOCUMENTS

| | | | |
|---|---|---|---|
| 4,618,617 | 10/1986 | Yamamoto | 546/277 |
| 5,086,053 | 2/1992 | Brodin et al. | 514/342 |
| 5,100,897 | 3/1992 | Allen et al. | 544/319 |
| 5,102,897 | 4/1992 | Boschelli et al. | 548/144 |

Primary Examiner—Marianne M. Cintins
Assistant Examiner—John Peabody
Attorney, Agent, or Firm—Ronald A. Daignault

[57] ABSTRACT

Heterocyclic methyl derivatives of biphenyl oxadiazoles and thiadiazoles are described, as well as methods for the preparation of said derivatives and pharmaceutical compositions of the same, which are useful as antagonists of the angiotensin II enzyme and thus useful in treating hypertension, hyperaldosteronism, congestive heart failure, and glaucoma.

11 Claims, No Drawings

BIPHENYL OXADIAZOLES AND THIADIAZOLES AS ANGIOTHESIN II ANTAGONISTS

The invention herein described relates to novel heteroalkyl biphenyl oxadiazoles and thiadiazoles useful as pharmaceutical agents, to methods for their production, to pharmaceutical compositions which include these compounds and a pharmaceutically acceptable carrier, and to pharmaceutical methods of treatment as well as the use of these agents as diagnostic tools. More particularly, the novel compounds of the present invention are antagonists of angiotensin II (AII) useful in controlling hypertension, hyperaldosteronism, congestive heart failure, and glaucoma in mammals.

The enzyme renin acts on a blood plasma $\alpha_2$-globulin, angiotensinogen, to produce angiotensin I, which is then converted by angiotensin converting enzyme to AII. The latter substance is a powerful vasopressor agent which has been implicated as a causative agent for producing high blood pressure in various mammals, such as rats, dogs, and humans. The compounds of this invention inhibit the action of AII at its receptors on target cells and thus prevent the increase in blood pressure produced by this hormone receptor interaction. By administering a compound of the instant invention to a species of mammal with hypertension due to AII, the blood pressure is reduced. The compounds of the invention are also useful for the treatment of congestive heart failure, hyperaldosteronism, and glaucoma.

SUMMARY OF THE INVENTION

Accordingly, the invention is a compound of the formula

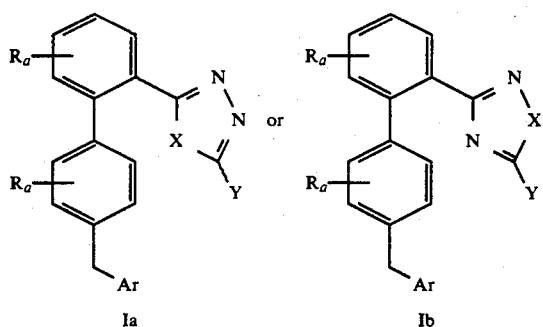

wherein
Ra is independently hydrogen, lower alkyl, lower alkoxy, or halo;
X is oxygen or sulfur;
Y is OH or SH, and
Ar is selected from the group consisting of

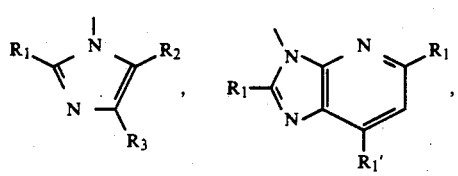

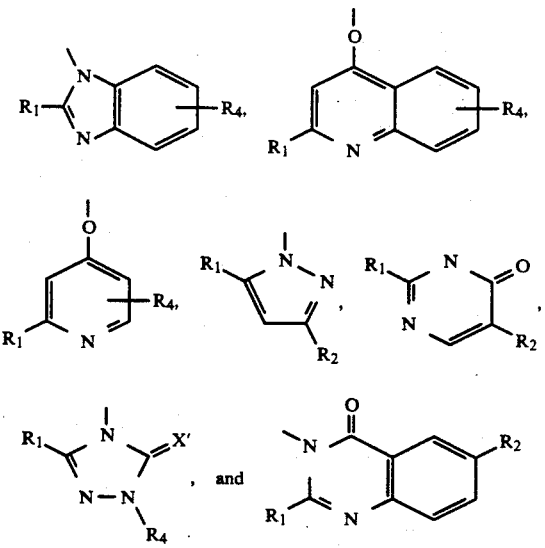

wherein X' is oxygen or sulfur; $R_1$ and $R_1'$ are each independently a lower alkyl group; $R_2$ is $CH_2OH$, CHO, or $CO_2R_4$; $R_3$ is hydrogen, halo, or a pyrrole group attached at the nitrogen atom and unsubstituted or substituted by lower alkyl, and $R_4$ is hydrogen or lower alkyl;

a tautomer thereof and a pharmaceutically acceptable salt thereof.

Angiotensin II mediates a variety of responses in various tissues, including contraction of vascular smooth muscle, excretions of salt and water from kidney, release of prolactin from pituitary, stimulation of aldosterone secretion from adrenal gland, and possible regulation of cell growth in both cardiac and vascular tissue. As antagonists of angiotensin II, the compounds of Formula I are useful in controlling hypertension, hyperaldosteronism, and congestive heart failure in mammals. Additionally, antihypertensive agents as a class have been shown to be useful in lowering intraocular pressure. Thus, the compounds of Formula Ia or Ib are also useful in controlling glaucoma.

A still further embodiment of the present invention is a pharmaceutical composition for administering an effective amount of a compound of Formula Ia or Ib in unit dosage form in the treatment methods mentioned above.

Finally, the present invention is directed to methods for production of a compound of Formula Ia or Ib.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n propyl, isopropyl, n-butyl, sec-butyl, isobutyl, tert-butyl, n-pentyl, n-hexyl, and the like.

"Lower alkoxy" is 0-alkyl of from one to six carbon atoms as defined above for "lower alkyl."

"Halogen" is fluorine, chlorine, bromine, or iodine.

The compounds of Formula I are capable of further forming both pharmaceutically acceptable acid addition and/or base salts. All of these form a are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxyalkanoic acids, alkanedioic acids, aromatic acids, aliphatic and aromatic sulfonic acids, etc. Such salts thus include hydrochloride, hydrobromide, hydroiodide, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science* 66:1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N-dibenzylethylenediamine, chloroprocaine, choline, diethanolamine, ethylenediamine, N methylglucamine, and procaine (see, for example, Berge, S. M., et al., "Pharmaceutical Salts," *Journal of Pharmaceutical Science* 66:1–19 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention can exist in tautomeric forms and such forms are included within the scope of the present invention. For example, a compound of the Formula Ia and its tautomeric form are illustrated as follows and is formed by shifting of a hydrogen atom.

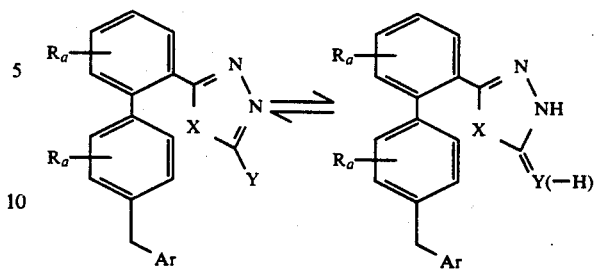

Similarly, a compound of the Formula Ib and its tautomer are shown as follows:

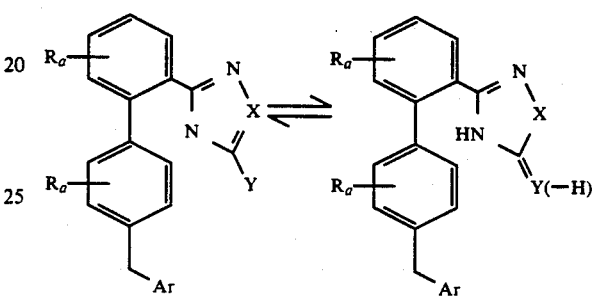

A preferred embodiment of the present invention is a compound of the formula

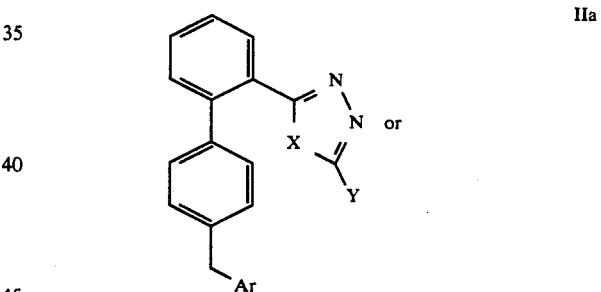

IIa

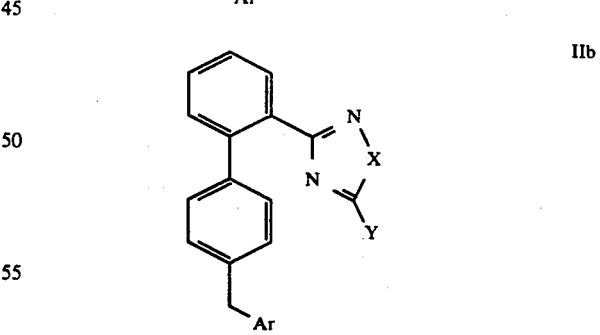

IIb wherein X, Y, and Ar are as defined above.

A more preferred embodiment is a compound of the Formula IIa or IIb wherein X, X', Y, and Ar are as defined above i which $R_1$ and $R_1'$ are lower alkyl; $R_2$ is $CH_2OH$, $CHO$, $CO_2H$, or $CO_2CH_3$; $R_3$ is hydrogen, chloro, or a pyrrole group attached at the nitrogen atom, and $R_4$ is hydrogen or lower alkyl.

Most preferred is a compound of Formula IIa or IIb wherein X and Y are as defined above, and Ar is

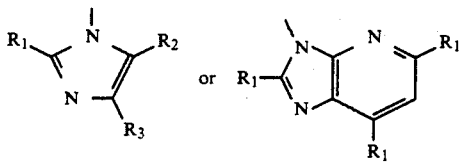

in which $R_1$ is lower alkyl; $R_2$ is $CH_2OH$, CHO, $CO_2H$, or $CO_2H_3$, and $R_3$ is hydrogen, chloro, or a pyrrole group attached at the nitrogen atom.

Particularly valuable are:

5-[4'-[5,7-Dimethyl-2-ethyl-3H-imidazo[4,5-b]pyridin-3-yl]methyl][1,1'-biphenyl-2-yl]-1,3,4-oxadiazol-2[3H]-one;

5-[4'-[5,7-Dimethyl-2-ethyl-3H-imidazo[4,5-b]pyridin-3-yl]methyl[1,1'-biphenyl-2-yl]-1,3,4-oxadiazol-2[3H]-thione;

5-[4'-[5,7-Dimethyl-2-ethyl-3H-imidazo[4,5-b]pyridin-3-yl]methyl][1,1'-biphenyl-2-yl]-1,3,4-thiadiazol-2[3H]-one;

5-[4'-[5,7-Dimethyl-2-ethyl-3H-imidazo[4,5-b]pyridin-3-yl]methyl][1,1'-biphenyl-2-yl]-1,3,4-thiadiazol-2[3H]-thione;

3-[4'-[5,7-Dimethyl-2-ethyl-3H-imidazo[4,5-b]pyridin-3-yl]methyl][1,1'-biphenyl-2-yl]-1,2,4-oxadiazol-5[4H]-one;

5-[4'-[2-Butyl-4-chloro-5-(hydroxymethyl)-1H-imidazol-1-yl]methyl][1,1'-biphenyl-2-yl]-1,3,4-oxadiazol-2[3H]-thione; and 5-[4'-[2-Butyl-4-chloro-5-(hydroxymethyl)-1H-imidazol-1-yl]methyl][1,1'-biphenyl-2-yl]-1,3,4-oxadiazol-2[3H]-one.

Most valuable are:

5-[4'-[5,7-Dimethyl-2-ethyl-3H-imidazo[4,5-b]pyridin-3-yl]methyl][1,1'-biphenyl-2-yl]-1,3,4-oxadiazol-2[3H]-one and 5-[4'-[5,7-Dimethyl-2--ethyl-3H-imidazo[4,5-b]pyridin-3-yl]methyl][1,1'-biphenyl-2-yl]-1,3,4-oxadiazol-2[3H]-thione.

The compounds of the present invention are prepared by the following series of described reactions and illustrated by the following synthetic schemes.

The preferred route is through an intermediate 2 illustrated in Scheme I and using this key intermediate in Schemes II and III to prepare the compounds of Formula Ia. The compounds of Formula Ib are preferably prepared through the cyano intermediate 4 using Schemes V and VI.

The key intermediates 2 and 4 are prepared as illustrated in Scheme I which involve the reaction of known bromomethyl biphenyl compounds 1 and 3 by reaction with the appropriate heterocycle ArH in the presence of base. Such bases are, for example, sodium hydride, sodium carbonate, cesium carbonate, and the like. The reaction can also be carried out in a suitable solvent such as, for example, tetrahydrofuran (THF), dioxane, or dimethylformamide (DMF) at temperatures of −20° C. to room temperature.

The heterocyclic ArH compounds are either known or can be prepared by known methods. These known heterocyclics have been described in the following references:

J. Med. Chem. 33:1312–1336 (1990),
Ep 253310,
EP 399731,
EP 400974,
J. Med Chem. 34:2919 2922 (1991),
EP 399732,
EP 400835,
EP 412848,
EP 456442,
EP 453210,
EP 323841,
EP 409332,
EP 411507,
EP 419048,
EP 412594,
EP 411766, and references cited therein.

SCHEME I

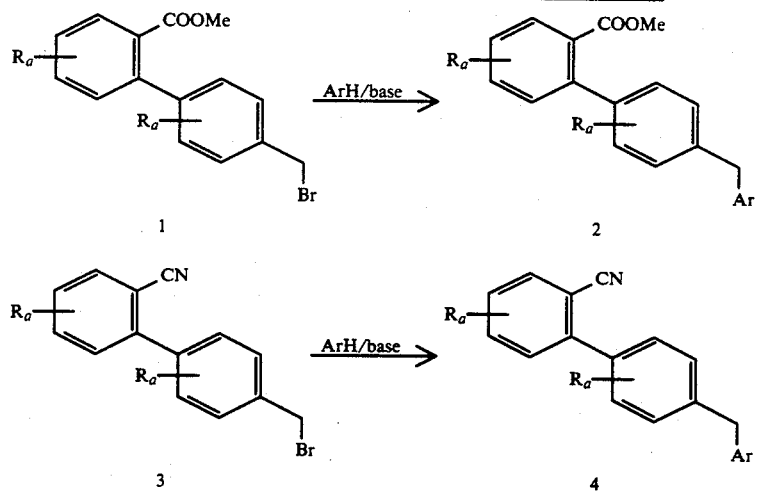

In certain cases it may be necessary to use known protecting groups on substituents of this heterocycle ArH which are then easily removable subsequent to the synthesis of the compounds 2 or 4. It also may be necessary in certain cases to separate regioisomeric alkylation products from intermediates 2 or 4 using standard separation techniques such as column chromatography.

The compounds of Formula Ia or Ib are then prepared using these key intermediates as illustrated in Schemes II to VI.

SCHEME II
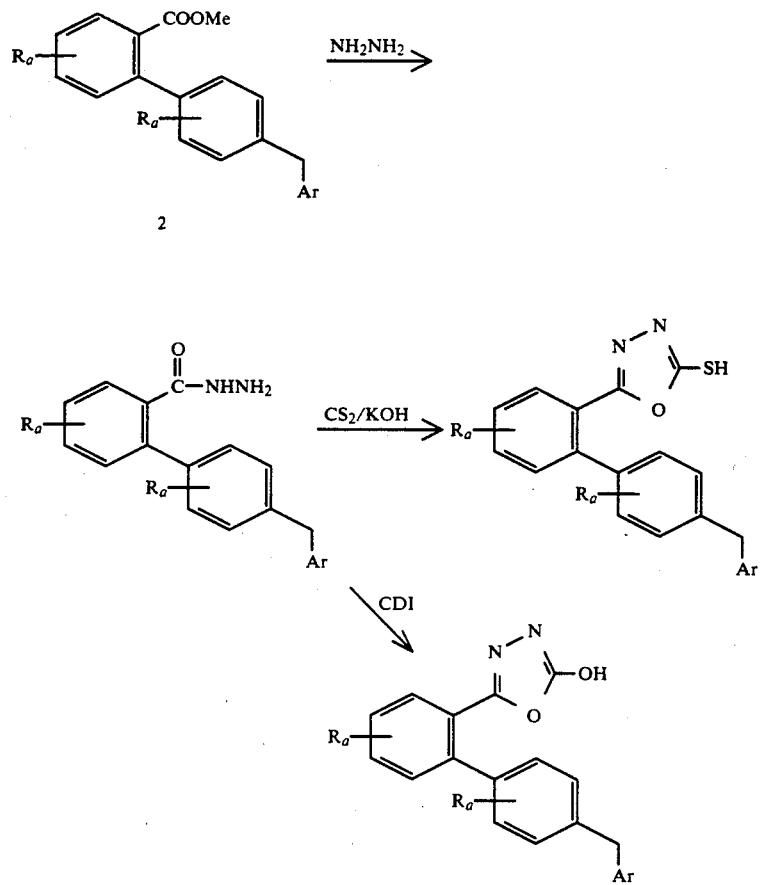
SCHEME III
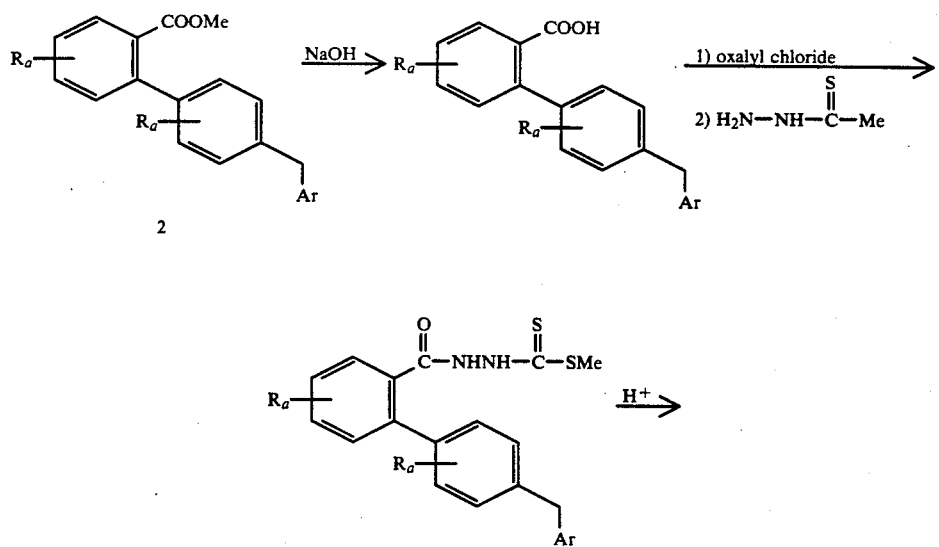

-continued
SCHEME III
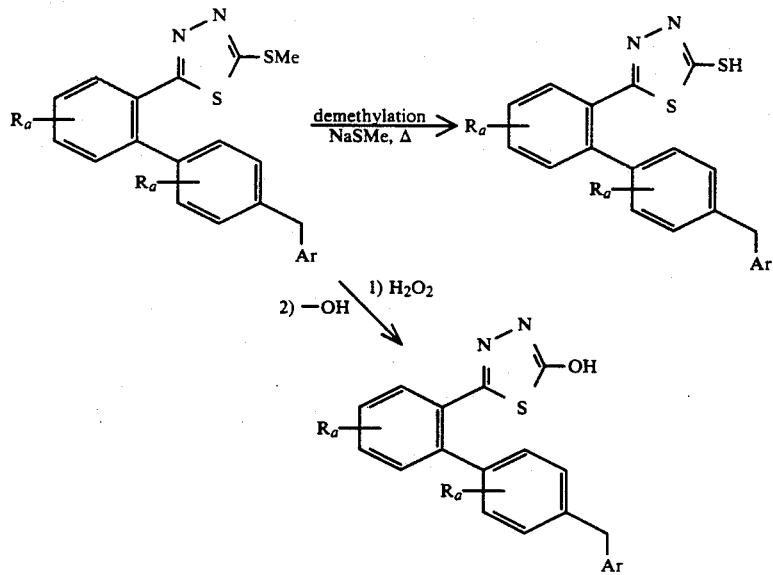
SCHEME IV
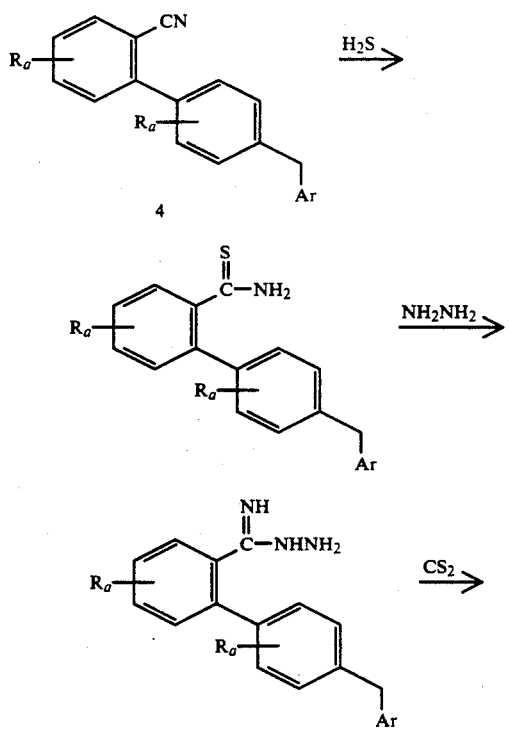
-continued
SCHEME IV
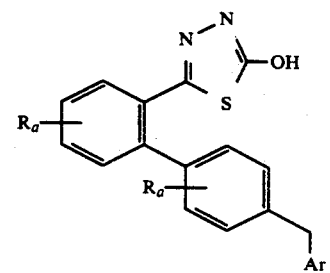

SCHEME V
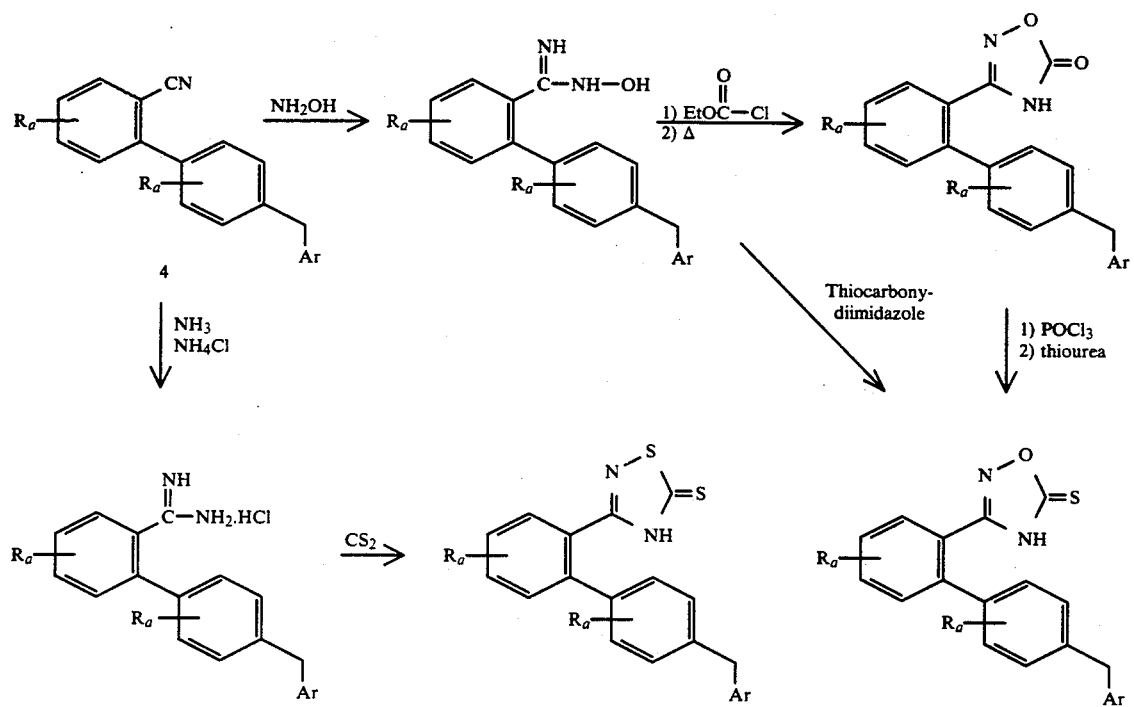
SCHEME VI
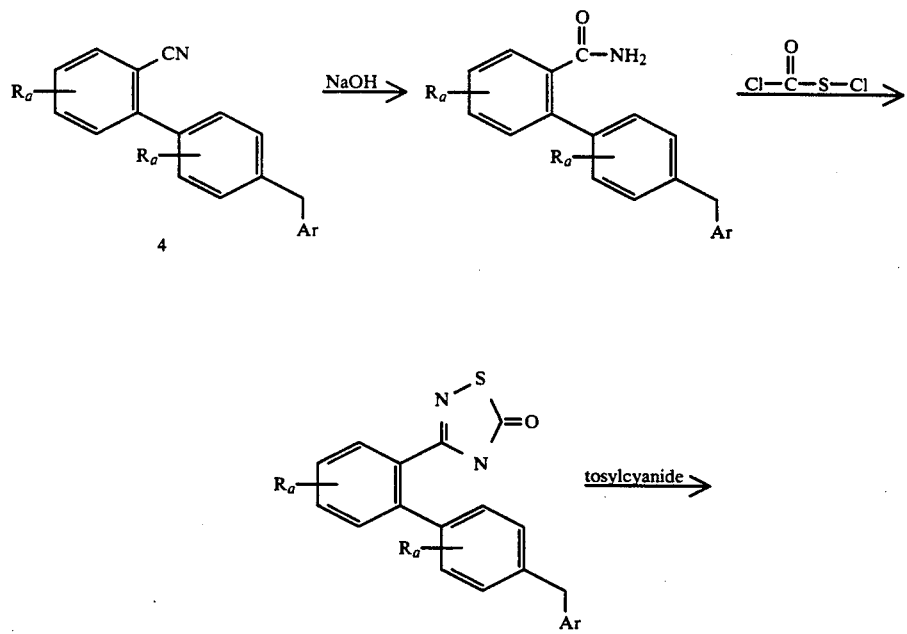

SCHEME VI

-continued

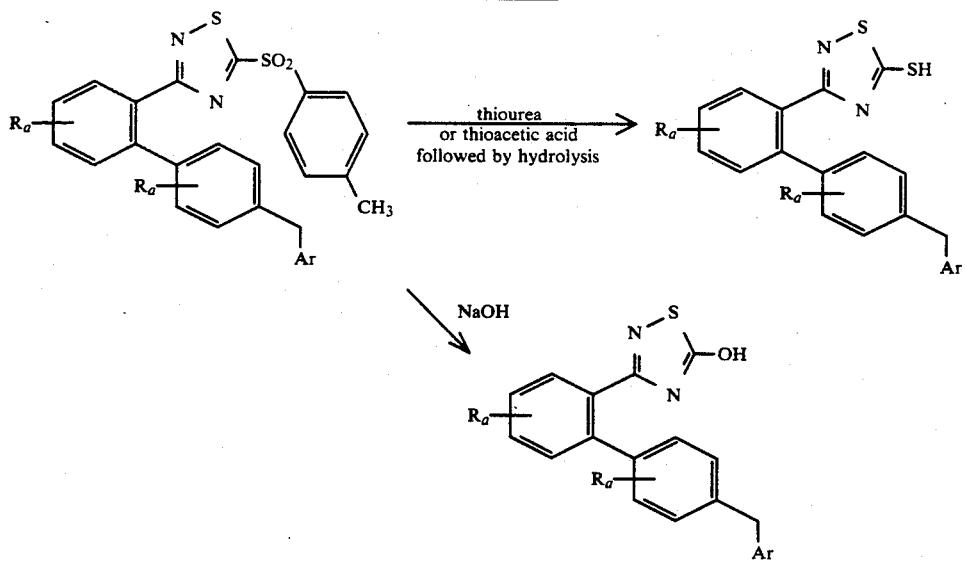

In Scheme II, the methyl ester of the heterocyclic biphenyl carboxylic acid is treated with hydrazine to form a hydrazide, which is then reacted with a carbon disulfide in the presence of base such as, for example, potassium hydroxide, to form a 2-mercapto-1,3,4-oxadiazole. Alternatively, the hydrazide can be treated with carbonyldiimidazole (CDI) to form a corresponding 2-hydroxy-1,3,4-oxadiazole.

In Scheme III, intermediate 2 is first treated with base such as sodium hydroxide to hydrolyze the ester followed by treatment with oxalylchloride and $H_2N$-NH $C(S)$-SMe to form the methylthioester hydrazide compound which is cyclized in acid conditions, e.g., aryl sulfonic acids or methanesulfonic acid in a solvent such as toluene at temperatures of 0° C. to reflux, to form the 2-thiomethyl-1,3,4-thiadiazole, which is demethylated under standard conditions such as with sodium thiomethoxide at elevated temperatures to form the desired 2-mercapto-thiadiazole or, alternatively, is oxidized with a reagent such as hydrogen peroxide or meta-chloro perbenzoic acid, followed by base hydrolysis to form the 2-hydroxy-1,3,4-thiadiazole.

In Scheme IV, intermediate 4, the heterocyclic biphenyl nitrile is treated with hydrogen sulfide to form the thioamide followed by treatment with hydrazine to form the imide hydrazone. Treatment of that compound with carbon disulfide, forms a cyclized product, the desired 2-mercapto 1,3,4 thiadiazole, which can be subsequently converted to the 2-hydroxy compound in three steps by treating first with methyl iodide, followed by hydrogen peroxide or meta-chloroperbenzoic acid and base hydrolysis.

In Scheme V, intermediate 4 is treated with hydroxylamine followed by ethyl chloroformate at elevated temperatures to form the compound of Formula Ib, in tautomeric form, namely the 5 oxo-1,2,4-oxadiazole. Alternatively, the product obtained with hydroxylamine is treated with thiocarbonyldiimidazole to form the 5-thiono 1,2,4-oxadiazole. Alternatively, intermediate 4 is treated with ammonia and ammonium chloride to form the amidine which, on treatment with carbon disulfide, gives the 5-thiono-1,2,4 thiazole.

In Scheme VI, intermediate 4 is treated with sodium hydroxide to form the amide followed by chlorocarbonyl sulfenyl chloride to form a 2-oxo-1,3,4-oxathiazole which decomposes to an intermediate nitrile sulfide which reacts with tosyl cyanide to give the 5-tosyl 1,2,4-thiadiazole, which on treatment with aqueous base provides the 5 hydroxy-1,2,4-thiadiazole. Alternatively, treatment of the tosyl compound with thiourea or thioacetic acid followed by hydrolysis yields the 5-mercapto-1,2,4-thiadiazole.

The compounds of Formula Ia or Ib can alternatively be prepared by constructing the thiadiazole or oxadiazole ring first followed by reaction with the desired heterocyclic ArH, as shown in Schemes VII through IX.

SCHEME VII

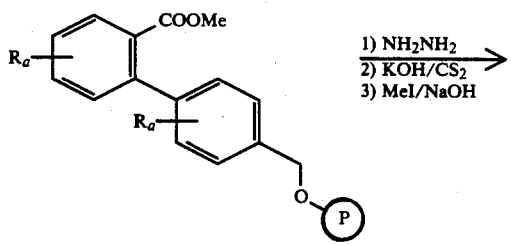

1) $NH_2NH_2$
2) $KOH/CS_2$
3) MeI/NaOH where —Ⓟ is a suitable protecting group

SCHEME VII
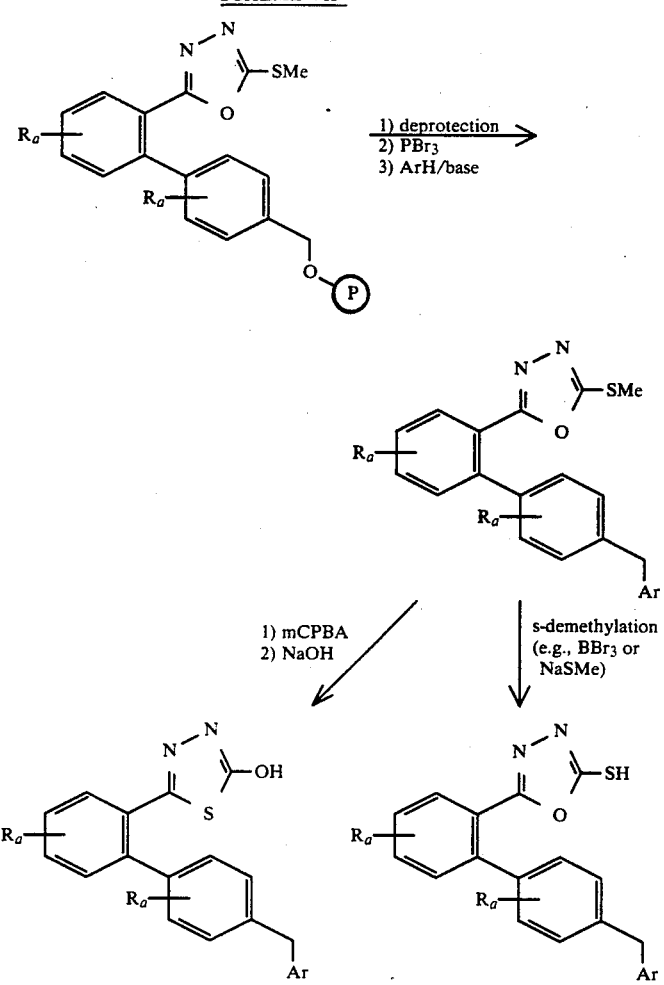
SCHEME VIII
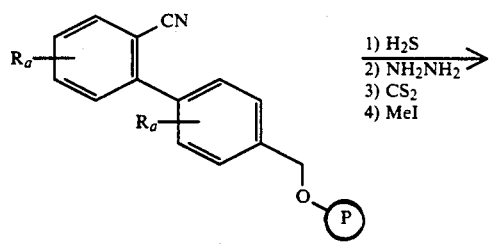
where —Ⓟ is a suitable protecting group
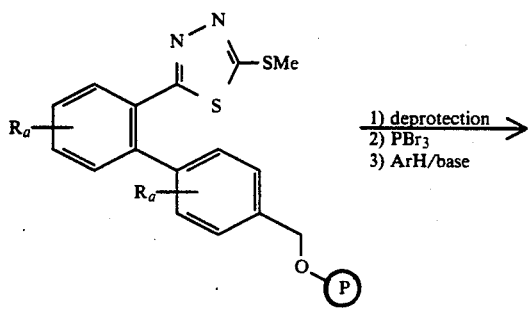

SCHEME VIII
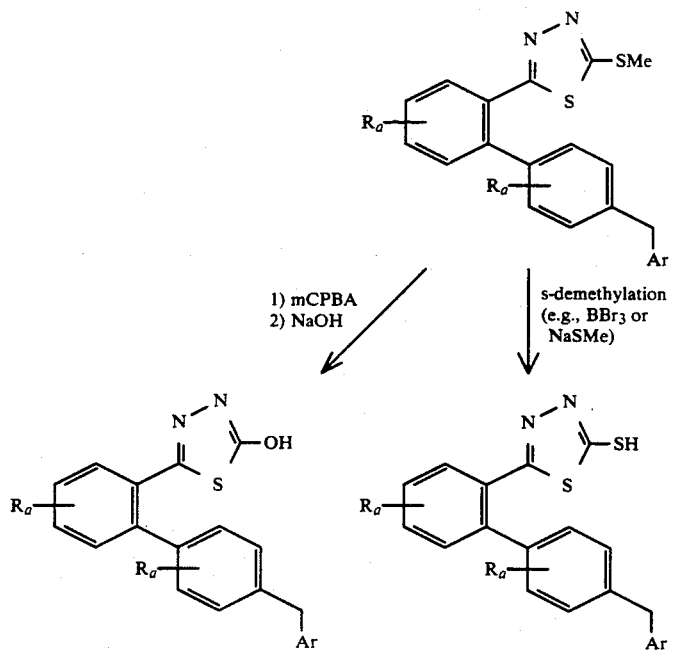
SCHEME IX
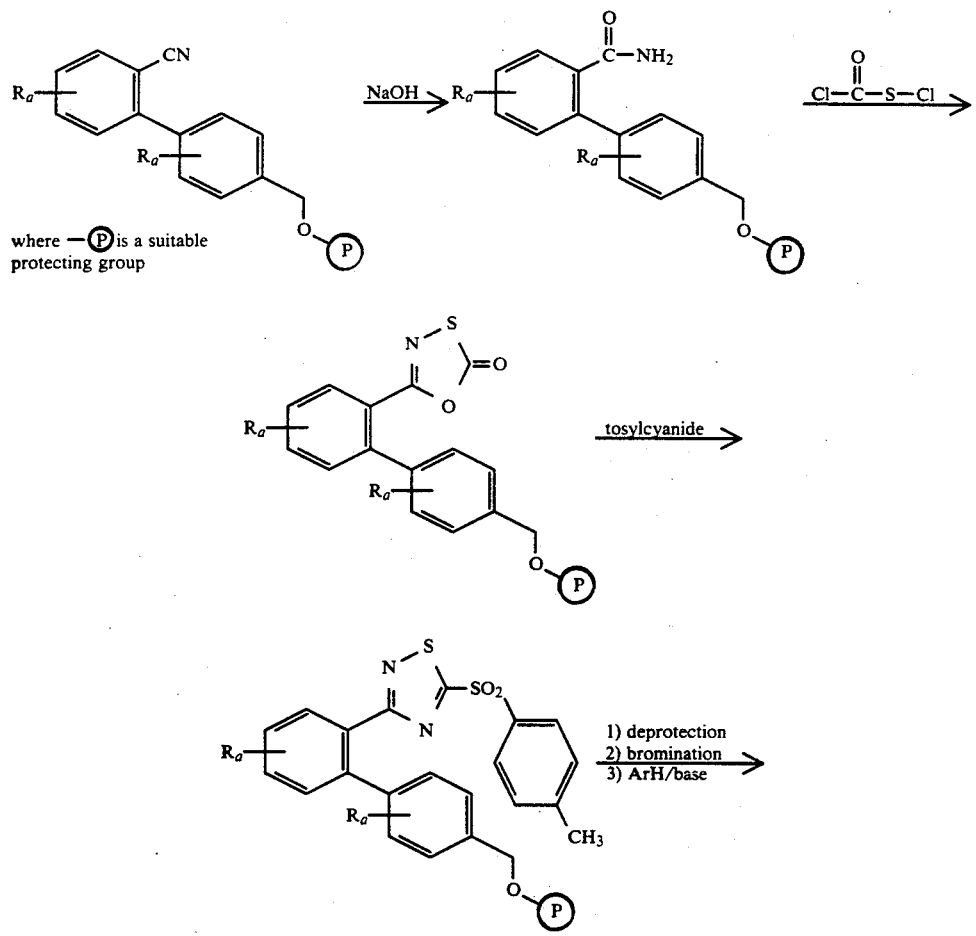

SCHEME IX -continued

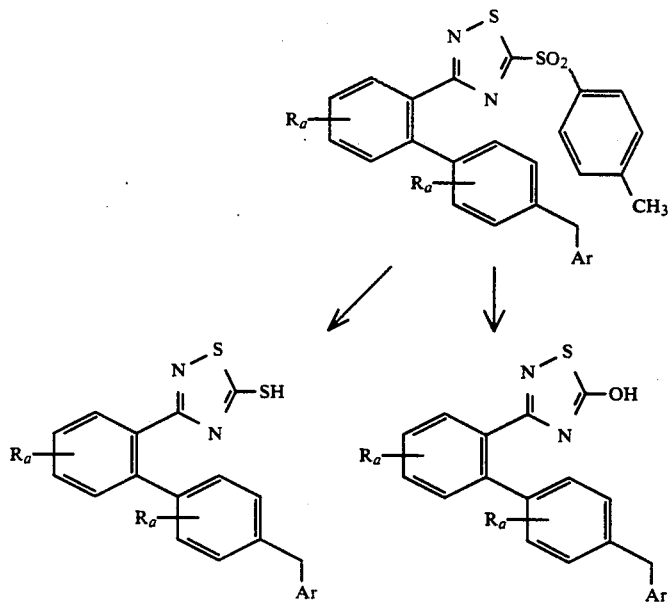

In Schemes VII through IX the key intermediates are compounds similar to compounds of formulae 2 and 4 where instead of the bromomethyl biphenyl compound a hydroxymethyl biphenyl carboxylic acid methyl ester or cyano compound is used where the hydroxyl group is protected with a suitable protecting group such as, for example, tetrahydropyranyl ether.

In Scheme VII, the methyl ester of the biphenyl carboxylic acid is treated in a similar manner as previous schemes to form either the 2-mercapto or 2-hydroxy-1,3,4-oxadiazoles where the heterocyclic group is placed following the formation of a 2-methylmercapto-1,3,4-thiadiazole compound by removing the hydroxyl protecting group according to known methods, for example, by treatment of the hydroxyl group with phosphorous tribromide and displacing the bromide with the desired heterocyclic compound in the presence of base in a similar manner as in the preparation of the key intermediates in Scheme I.

Scheme VIII illustrates the same kind of preparation incorporating the heterocyclic followed by the preparation of the thiadiazole.

Scheme IX begins with a biphenyl nitrile compound having a protected hydroxyl. Treatment with sodium hydroxide forms a corresponding amide which is then treated with chlorocarbonyl sulfenyl chloride to form a 5-oxo 1,3,4-oxathiazole, which is treated with tosyl cyanide as shown previously in Scheme VI. At this stage, the hydroxyl group on the biphenyl is deprotected, brominated, and displaced with the desired heterocyclic moiety as described above. The tosyl intermediate with a heterocyclic moiety attached is then converted either to the 5-mercapto- 1,2,4-thiadiazole or the 5-hydroxy-1,2,4-thiadiazole, as described again previously in Scheme VI.

The effectiveness of the compounds of the instant invention is determined by a test (RBAT) entitled Receptor Binding of Angiotensin II. The test method is described by Dudley, D. T., et al, *Molecular Pharmacology* 38:370–377 (1990). In this in vitro test the inhibition of tritiated angiotensin II binding to rat liver membranes is measured. The data in the following table show the binding activity of representative compounds of the invention.

TABLE

| Example | RBAT ($\mu$M) |
| --- | --- |
| 3 | 0.09 |
| 4 | 0.006 |
| 9 | 0.6 |
| 10 | 6 |

Based on the observations that ACE inhibitors are known to benefit patients with heart failure, the instant compound which also interrupts the renin angiotensin system (RAS), would show similar benefits.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents. It can also be encapsulating material. In powders, the carrier is a finely divided solid which is in admixture with the finely divided active compound. In the tablet the active compound is mixed with a carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compounds of the present invention may be administered orally, buccally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquified form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethyl cellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerin, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient.

The compositions can, if desired, also contain other compatible therapeutic agents.

In therapeutic use as renin inhibitors, the mammalian dosage range for a 70 kg subject is from 0.1 to 1500 mg/kg of body weight per day or preferably 1 to 500 mg/kg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

4'-[[5,7-Dimethyl-2-ethyl-3H-imidazo[4,5-b]pyridin-3yl]methyl][1,1'-biphenyl-2-yl]carboxylic acid methyl ester To a suspension of sodium hydride (345 mg, 60% in oil, 8.6 mmol) in dry DMF (10 mL) was added 5,7-dimethyl-2-ethylimidazo[4,5-b]pyridine (1.5 g, 8.6 mmol) under an atmosphere of dry nitrogen. The reaction mixture was stirred at room temperature until the evolution of gas subsided. The reaction mixture was cooled to 0° C. and a solution of methyl 4'-bromomethylbiphenyl-2-carboxylate (2.7 g, 8.84 mmol) in dry DMF (5 mL) was added dropwise. The resulting solution was stirred at room temperature overnight. The reaction mixture was poured into water (250 mL), the pH was adjusted to pH 6 by the addition of 1N HCl, and the product was extracted into ethyl acetate. Flash chromatography (silica, ethyl acetate) gave 4'-[[5,7-dimethyl-2-ethyl-3H-imidazo[4,5-b]pyridin-3-yl]methyl][1,1'-biphenyl-2-yl]carboxylic acid methyl ester (2.05 g, 61%) as an amorphous solid.

EXAMPLE 2

4'-[[5,7-Dimethyl-2-ethyl-3H-imidazo[4,5-b]pyridin-3-yl]methyl]1,1'-biphenyl-2-yl]carboxylic acid hydrazide A solution of 4'-[[5,7-dimethyl-2-ethyl-3H-imidazo[4,5-b]pyridin-3-yl]methyl[1,1'-biphenyl-2-yl]carboxylic acid methyl ester (1.3 g) and hydrazine hydrate (8 mL) in methanol (20 mL) was heated at reflux overnight under a nitrogen atmosphere. The reaction mixture was concentrated to 10 mL under reduced pressure and diluted with water. The resulting precipitate was collected by filtration, washed with water, and dried under vacuum overnight. Recrystallization from ethyl acetate gave pure 4'-[[5,7-dimethyl-2-ethyl-3H-imidazo[4,5 b]pyridin-3yl]methyl][1,1'-biphenyl-2-yl]carboxylic acid hydrazide (1.2 g, 96%) as a monohydrate, mp 139°-142° C.

Analysis calculated for $C_{24}H_{25}N_5O \cdot H_2O$: C, 69.04; H, 6.52; N, 16.82. Found: C, 69.20; H, 6.32; N, 16.67.

EXAMPLE 3

5-[4'-[[5,7-Dimethyl-2-ethyl-3H-imidazo[4,5-b]pyridin-3-yl]methyl][1,1'-biphenyl-2-yl]-1,3,4-oxadiazol-2[3H]-one To a solution of 4'-[[5,7-dimethyl-2-ethyl-3H-imidazo[4,5-b]pyridin-3-yl]methyl][1,1'-biphenyl-2-yl]carboxylic acid hydrazide (400 mg, 1 mmol) and triethylamine (130 mg, 1.3 mmol) in THF (20 mL) was added carbonyldiimidazole (275 mg, 1.7 mmcl) at 0° C. The reaction mixture was stirred at room temperature overnight and the solvent was evaporated. The residue was dissolved in water and the solution was adjusted to pH 3 by the addition of IN HCl. The resulting precipitate was collected by filtration and dried under vacuum to give 5- [4'-[[5,7-dimethyl-2-ethyl-3H-imidazo[4,5-b]pyridin 3-yl]methyl][1,1'-biphenyl-2-yl]-1,3,4 oxadiazol-2[3H]-one (0.35 g, 81%) as a partial hydrate, mp 210°–212° C.

Analysis calculated for $C_{25}H_{23}N_5O_20.4H_2O$: C, 69.39; H, 5.54; N, 16.19. Found: C, 69.43; H, 5.54; N, 16.16.

EXAMPLE 4

5- [4'-[[5,7-Dimethyl-2-ethyl-3H-imidazo[4,5 b]pyridin-3-yl]methyl][1,1'-biphenyl-2-yl]-1,3,4-oxadiazol-2[3H]-thione A solution of 4'-[5,7-dimethyl-2-ethyl-3H-imidazo[4,5-b]pyridin-3-yl]methyl][1,1'-biphenyl-2-yl]carboxylic acid hydrazide (400 mg, 1 mmol), and KOH (56 mg, 1 mmol), and carbon disulfide (0.18 mL) in methanol (20 mL) was heated at reflux overnight. The reaction mixture was cooled and evaporated. The residue was dissolved in water (20 mL) and the resulting solution was acidified to pH 3. The solid was collected by filtration, washed with water, and dried under vacuum to give 5-[4'-[[5,7-dimethyl-2-ethyl-3H-imidazo[4,5-b]pyridin-3-yl]methyl][1,1'-biphenyl-2-yl]-1,3,4-oxadiazol-2[3H]-thione (0.33 g, 73%) as a partial hydrate, mp 260°–268° C. dec.

Analysis calculated for $C_{25}H_{23}N_5OS.1/2H_2O$: C, 66.64; H, 5.37; N, 15.54. Found: C, 66.84; H, 5.39; N, 15.40.

EXAMPLE 5

4'-[[2-Butyl-4-chloro-5-(t-butyldimethylsilyloxymethyl)-1H-imidazol-1-yl]methyl][1,1'-biphenyl-2-yl]carboxylic acid methyl ester A solution of methyl 4'-bromomethylbiphenyl-2-carboxylate (2.05 g) in dry THF (10 mL) was added dropwise to a solution of 2-butyl-4-chloro-5-(t-butyldimethylsilyloxymethyl)-1H-imidazole (2.03 g) and NaN(TMS)$_2$ (1.48 g) in dry THF (20 mL) at 0° C. and the reaction mixture was stirred at room temperature overnight. It was diluted with brine and the organic layer was collected, dried over MgSO$_4$, and evaporated under reduced pressure. The residue was purified by flash chromatography (EtOAc, silica) to separate the two regioisomeric alkylation products. The major isomer, 4'-[[2-butyl-4 chloro-5-(t-butyldimethylsilyloxymethyl) 1H-imidazol-1-yl]methyl][1,1'-biphenyl-2-yl]carboxylic acid methyl ester (1.4 g) was used in the next step and the regiochemistry of this alkylation product was proven by NOE experiments at the stage of the hydrazide.

EXAMPLE 6

4'-[2-Butyl-4-chloro-5-(t-butyldimethylsilyloxymethyl)-1H-imidazol-1-yl]methyl][1,1'-biphenyl-2-yl]carboxylic acid hydrazide According to the procedure of Example 2, 4'-[[2-butyl-4-chloro-5-(t-butyldimethylsilyloxymethyl)-1H-imidazol-1-yl]methyl][1,1'-biphenyl-2-yl]carboxylic acid methyl ester was treated with hydrazine to give 4'-[[2-butyl-4-chloro-5-(t-butyldimethylsilyloxymethyl)-1H imidazol-1-yl]methyl][1,1'-biphenyl-2-yl]carboxylic acid hydrazide (60%).

EXAMPLE 7

5-[4'-[[2-Butyl-4-chloro-5-(t-butyldimethylsilyloxymethyl)-1H-imidazol-1-yl]methyl][1,1'-biphenyl-2-yl]-1,3,4-oxadiazol-2[3H-one According to the procedure of Example 3, 4'-[[2-butyl-4-chloro-5-(t butyldimethylsilyloxymethyl)-1H-imidazol-1-yl]methyl][1,1'-biphenyl-2-yl]carboxylic acid hydrazide was treated with triethylamine and carbonyldiimidazole to give 5-[4'-[[2-butyl-4-chloro-5-(t-butyldimethylsilyloxymethyl)-1H-imidazol-1yl]methyl][1,1 -biphenyl-2-yl]-1,3,4-oxadiazol-2[3H]one (80%).

EXAMPLE 8

5-[4'-[[2-Butyl-4-chloro-5-(t-butyldimethylsilyloxymethyl)-1H-imidazol-1-yl]methyl][1,1'-biphenyl-2-yl]-1,3,4-oxadiazol-2[3H]-thione According to the procedure of Example 4, 4'-[[2-butyl-4-chloro-5-(t-butyldimethylsilyloxymethyl)-1H-imidazol-1-yl]methyl][1,1'-biphenyl-2-yl]carboxylic acid hydrazide was treated with KOH and carbon disulfide to give 5-[4'-[[2-butyl-4-chloro-5-(t-butyldimethylsilyloxymethyl)-1H-imidazol 1-yl]methyl][1,1'-biphenyl-2-yl]-1,3,4-oxadiazol-2[3H]thione (70%).

Analysis calculated for $C_{29}H_{37}ClN_4O_2Si$: C, 61.19; H, 6.55; N, 9.84. Found: C, 60.78; H, 6.33; N, 9.79.

EXAMPLE 9

5-[4'-[[2-Butyl-4-chloro-5-(hydroxymethyl)-1H-imidazol-1-yl]methyl][1,1'-biphenyl-2-yl]-1,3,4-oxadiazol-2[3H]-thione A solution of 5-[4'-[[2-butyl-4-chloro-5-(t-butyldimethylsilyloxymethyl)-1H-imidazol-1-yl]methyl][1,1'-biphenyl-2-yl]-1,3,4-oxadiazol-2[3H]-thione (100 mg) in 1:9 48% HF/acetonitrile (10 mL) was stirred at room temperature for 3 hours in a plastic flask. The reaction mixture was neutralized by the dropwise addition of saturated aqueous NaHCO$_3$ (to pH 5) and was diluted with water. The resulting precipitate was collected by filtration and washed with water. Recrystallization from ethyl acetate gave pure 5-[4'-[[2-butyl-4-chloro-5-(hydroxymethyl)1H imidazol-1-yl]methyl][1,1'-biphenyl-2-yl]-1,3,4-oxadiazol-2[3H]-thione (40 mg, 50%), mp 193°–194° C. dec.

Analysis calculated for $C_{23}H_{23}ClN_4O_2S$: C, 60.72; H, 5.10; N, 12.31. Found: C, 60.66; H, 4.99; N, 12.24.

EXAMPLE 10

5-[4'-2-Butyl-4-chloro-5--(hydroxymethyl)-1H-imidazol-1-yl]methyl][1,1'-biphenyl-2-yl]-1,3,4-oxadiazol-2[3H]one According to the procedure of Example 9, 5-[4'-[[2-butyl-4-chloro-5-(t-butyldimethylsilyloxymethyl)-1H- imidazol-1-yl]methyl][1,1'-biphenyl-2-yl]-1,3,4-oxadiazol-2[3H]-one (170 mg) was treated with HF. Recrystallization from hexane/ethyl acetate gave pure 5-[4'-[[2-butyl-4-chloro-5-(hydroxymethyl)-1H-imidazol-1-yl]methyl][1,1'-biphenyl-2-yl]-1,3,4-oxadiazol-2[3H]-one (100 mg, 75%), mp 158°–159° C.

Analysis calculated for $C_{23}H_{23}ClN_4O_3$: C, 62.94; H, 5.28; N, 12.76. Found: C, 62.93; H, 5.28; N, 12.65.

We claim:

1. A compound of the formula

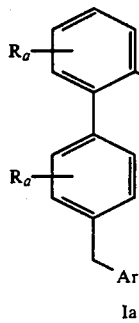 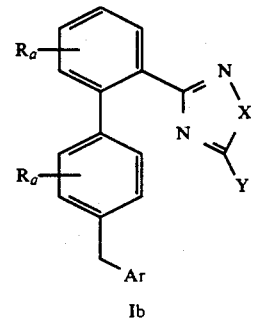

wherein
$R_a$ is independently hydrogen, lower alkyl, lower alkoxy, or halo;
X is oxygen or sulfur;
Y is OH or SH, and
Ar is selected form the group consisting of

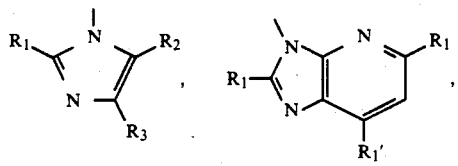

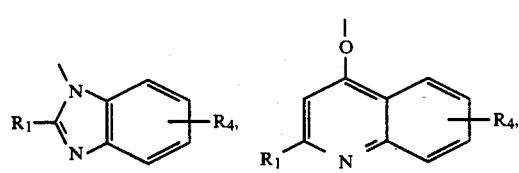

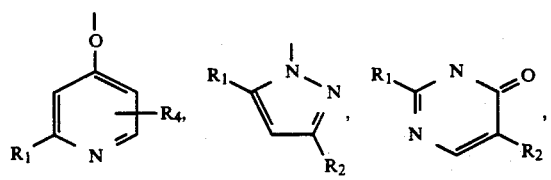

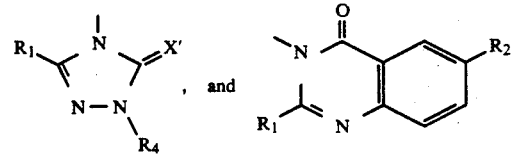

wherein X' is oxygen or sulfur; $R_1$ and $R_1'$ are each independently lower alkyl; $R_2$ is $CH_2OH$, CHO, or $CO_2R_4$; $R_3$ is hydrogen, halo, or a pyrrole group attached at the nitrogen atom and unsubstituted or substituted by lower alkyl, and $R_4$ is hydrogen or lower alkyl;

a tautomer thereof and a pharmaceutically acceptable salt thereof.

2. A compound according to claim 1 and of the formula

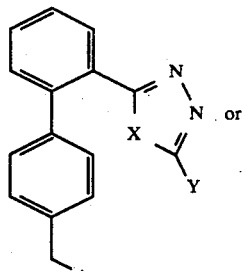

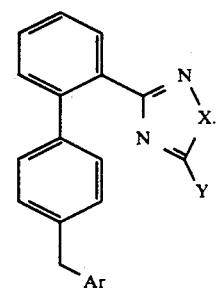

3. A compound according to claim 2 i which $R_1$ and $R_1'$ are each independently lower alkyl; $R_2$ is $CH_2OH$, CHO, $CO_2H$, or $CO_2CH_3$; $R_3$ is hydrogen, chloro, or a pyrrole group attached at the nitrogen atom, and $R_4$ is hydrogen or lower alkyl.

4. A compound according to claim 3 wherein Ar is

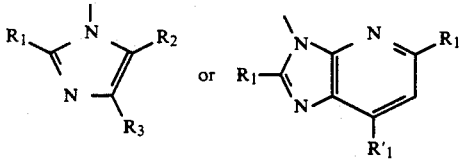

in which $R_1$ and $R_1'$ are each independently lower alkyl; $R_2$ is $CH_2OH$, CHO, $CO_2H$, or $CO_2H_3$, and $R_3$ is hydrogen, chloro, or a pyrrole group attached at the nitrogen atom.

5. A compound according to claim 4 and being 5-[4'-[5,7-dimethyl-2-ethyl-3H-imidazo[4,5-b]pyridin-3-yl]methyl][1,1'-biphenyl-2-yl]-1,3,4-oxadiazol-2[3H]-one.

6. A compound according to claim 4 and being 5-[4'-[5,7-dimethyl-2-ethyl-3H-imidazo[4,5-b]pyridin-3-yl]methyl][1,1'-biphenyl-2-yl]-1,3,4-oxadiazol-2[3H]thione.

7. A compound according to claim 4 and being 5-[4'-[5,7-dimethyl-2-ethyl-3H-imidazo[4,5-b]pyridin-3-yl]methyl][1,1'-biphenyl-2-yl]-1,3,4-thiadiazol-2[3H]-one.

8. A compound according to claim 4 and being 5-[4'-[5,7-dimethyl-2-ethyl-3H-imidazo[4,5-b]pyridin-3-yl]methyl][1,1'-biphenyl-2-yl]-1,3,4-thiadiazol-2[3H]-thione.

9. A compound according to claim 4 and being 3-[4'-[5,7-dimethyl-2-ethyl 3H-imidazo[4,5-b]pyridin-3-yl]methyl[1,1'-biphenyl-2-yl]-1,2,4-oxadiazol-5[4H]-one.

10. A compound according to claim 4 and being 5-[4'-[2-butyl-4-chloro-5-(hydroxymethyl)-1H-imidazol 1-yl]methyl][1,1'-biphenyl-2-yl]-1,3,4-oxadiazol-2[3H]-thione.

11. A compound according to claim 4 and being 5-[4'-[2-butyl-4-chloro-5-(hydroxymethyl)-1H-imidazol-1-yl]methyl][1,1'-biphenyl-2-yl]-1,3,4-oxadiazol-2[3H]-one.

* * * * *